United States Patent
Papagiannakis et al.

(10) Patent No.: US 12,002,573 B2
(45) Date of Patent: Jun. 4, 2024

(54) COMPUTER CLASSIFICATION OF BIOLOGICAL TISSUE

(71) Applicant: DYSIS MEDICAL LIMITED, London (GB)

(72) Inventors: Emmanouil Papagiannakis, London (GB); Alastair Atkinson, London (GB)

(73) Assignee: DYSIS MEDICAL LIMITED, London (GB)

( * ) Notice: Subject to any disclaimer, the term of this patent is extended or adjusted under 35 U.S.C. 154(b) by 0 days.

(21) Appl. No.: 18/046,249

(22) Filed: Oct. 13, 2022

(65) Prior Publication Data

US 2023/0126691 A1    Apr. 27, 2023

Related U.S. Application Data

(63) Continuation of application No. 17/051,366, filed as application No. PCT/GB2019/052074 on Jul. 24, 2019, now Pat. No. 11,562,820.

(51) Int. Cl.
G06K 9/00 (2022.01)
G06T 7/00 (2017.01)
(Continued)

(52) U.S. Cl.
CPC ........... G16H 30/40 (2018.01); G06T 7/0012 (2013.01); G16H 50/20 (2018.01); G16H 50/30 (2018.01);
(Continued)

(58) Field of Classification Search
None
See application file for complete search history.

(56) References Cited

U.S. PATENT DOCUMENTS

2010/0092064 A1    4/2010    Li
2018/0129911 A1    5/2018    Madabhushi et al.
2021/0042915 A1    2/2021    Bernat et al.

FOREIGN PATENT DOCUMENTS

CN    101460090 A    6/2009
CN    102282569 A    12/2011
(Continued)

OTHER PUBLICATIONS

H.-G. Acosta-Mesa, F. Rechy-Ramírez, E. Mezura-Montes, N. Cruz-Ramírez, and R. Hernández-Jiménez, "Application of time series discretization using evolutionary programming for classication of precancerous cervical lesions," J. Biomed. Inform., vol. 49, pp. 73-83, (Year: 2014).*
(Continued)

*Primary Examiner* — Wei Wen Yang
(74) *Attorney, Agent, or Firm* — Stanek Lemon Crouse & Meeks, P.A.

(57) ABSTRACT

A biological tissue is classified using a computing system. Image data comprising a plurality of images of an examination area of a biological tissue is received at the computing system. Each of the plurality of images is captured at different times during a period in which topical application of a pathology differentiating agent to the examination area of the tissue causes transient optical effects. The received image data is provided as an input to a machine learning algorithm operative on the computing system. The machine learning algorithm is configured to allocate one of a plurality of classifications to each of a plurality of segments of the tissue.

26 Claims, 8 Drawing Sheets

(51) Int. Cl.
 *G16H 30/40* (2018.01)
 *G16H 50/20* (2018.01)
 *G16H 50/30* (2018.01)
(52) U.S. Cl.
 CPC .............. *G06T 2207/20076* (2013.01); *G06T 2207/20081* (2013.01); *G06T 2207/20084* (2013.01)

(56) References Cited

FOREIGN PATENT DOCUMENTS

| | | | |
|---|---|---|---|
| CN | 107274386 A | | 10/2017 |
| EP | 1978867 A2 | | 10/2008 |
| RU | 2288636 | | 12/2006 |
| RU | 2654199 | | 5/2018 |
| WO | 2010/042211 A1 | | 4/2010 |
| WO | 2011/139362 A1 | | 5/2011 |
| WO | 2018/018160 | | 2/2018 |

OTHER PUBLICATIONS

Xu et al., "Multimodal Deep Learning for Cervical Dysplasia Diagnosis." Oct. 2, 2016, International Conference on Computer Analysis of Images and Patterns; CAIP 2017: Computer Analysis of Images and Patterns; [Lecture Notes in Computer Science; Lect. Notes Computer], Springer, Berlin, Heidelberg, pp. 115-123, XP0473292489.

International Search Report and Written Opinion dated Oct. 9, 2019, in International Application No. PCT/GB2019/052074 with international filing date Jul. 24, 2019, 16 pages.

International Preliminary Report on Patentability dated Sep. 24, 2020, in International Application No. PCT/GB2019/052074 with international filing date Jul. 24, 2019, 8 pages.

Combined Search and Examination Report, GB 1812050.1, dated Jan. 2, 2019, 5 pages.

Official Action, Russian Patent Application No. RU2020138594/28, dated Jul. 7, 2021, 13 pages.

First Office Action, Chinese Patent Application No. 201980030130.0, dated May 27, 2021, 21 pages.

Fernandes, "Automated Methods for the Decision Support of Cervical Cancer Screening Using Digital Colposcopies," IEEE, May 2018, pp. 33910-33927, 2018.

Acosta-Mesa et al., "Aceto-white temporal pattern classification using k-NN to identify precancerous cervical lesion in colposcopic images," Computers in Biology and Medicine, 39, 2009, pp. 776-784.

Xu et al., "Multi-feature based benchmark for cervical dysplasia classification evaluation," Pattern Recognition, 63, 2017, pp. 468-475.

\* cited by examiner

COMPUTER CLASSIFICATION OF BIOLOGICAL TISSUE

CROSS-REFERENCE TO RELATED APPLICATIONS

This application is a continuation of U.S. application Ser. No. 17/051,366, filed Oct. 28, 2020, which is a 35 U.S.C. § 371 National Stage Entry of International Application No. PCT/GB2019/052074 having an international filing date of Jul. 24, 2019, which claims the benefit of Great Britain Application No. 1812050.1, filed Jul. 24, 2018, the contents of which are hereby incorporated herein by reference in their entireties.

TECHNICAL FIELD OF THE DISCLOSURE

The disclosure concerns classification of a biological tissue using a computing system, including a method and corresponding computer program and computer system.

BACKGROUND TO THE DISCLOSURE

Examination and classification of biological tissue is part of cancer screening procedures. For example in the case of screening for cervical cancer, a colposcopy can be performed, in which the cervix uteri is directly viewed and one or more images of it are captured. This allows lesions in the cervix uteri to be identified and classified, dependent on their risk, so that appropriate biopsies or treatment may be performed. Such classification is generally performed by medical professionals.

An especially well-performing colposcopy technique has been described in International Patent Publication number WO-01/72214, in which a pathology differentiating agent (especially dilute acetic acid) is applied to the biological tissue. This causes a transient optical effect, specifically a whitening of the tissue, which can be viewed directly and also in a captured image. Moreover, transient and/or spectral analysis of the one or more captured images, particularly measurement of diffuse reflectance, can be performed and such data can be provided to a medical professional to assist with their analysis. Colposcopes using this technique are marketed by Dysis Medical Limited.

Computer-based artificial intelligence has been applied to medical classifications in a number of areas, such as magnetic resonance imaging (MRI) and radiology images. The application of artificial intelligence technologies to classification of biological tissue, such as cervical lesion classification has also been considered. "An Observational Study of Deep Learning and Automated Evaluation of Cervical Images for Cancer Screening", Hu et al., J Natl Cancer Inst 2019 (doi: 10.1093/jnci/djy225) studied the automated evaluation of "cervigrams" (cervical images taken with a fixed-focus, ring-lit film camera, about a minute after application of dilute acetic acid to the cervical epithelium) to identify precancerous and cancerous lesions for point-of-care cervical screening. In this approach, a cervigram is provided as an input to a deep learning-based algorithm, specifically a faster region-based convolutional neural network (Faster R-CNN). The algorithm performs object (cervix) detection, feature extraction (calculating the features of the object) and classification as positive or negative for high-grade cervical neoplasia (predicting the case probability score). This method, when studied on a screening population, achieved an area under the curve (AUC) of 0.91, which was greater than the original cervigram interpretation (AUC of 0.69) of the same dataset, in identifying pre-cancer or cancer cases.

"Multimodal Deep Learning for Cervical Dysplasia Diagnosis", Xu et al., Medical Image Computing and Computer-Assisted Intervention—MICCAI 2016. Lecture Notes in Computer Science, vol. 9901, Springer, Cham, considers the application of machine learning to diagnosis of cervical dysplasia. In this approach, an image of a cervix captured subsequent to the application of 5% acetic acid to the cervical epithelium is provided as an input to a deep neural network. In additional, clinical results of other medical tests and other data regarding the subject are provided as inputs, such that the neural network has multimodal inputs. A structure involving multiple convolutional neural network layers is used for learning image features and the different modalities are combined using joint fully connected neural network layers. This technique is reported to give a final diagnosis with 87.83% sensitivity at 90% specificity.

Such techniques can be useful to medical professionals, especially in the developing world where cervical screening is not available, but the provision of more clinically useful outputs from artificial intelligence, such as the mapping and grading of disease for accurate biopsy placement, are desirable to improve the ability of the medical professional to diagnose correctly and provide suitable treatment or follow up if needed.

SUMMARY OF THE DISCLOSURE

Against this background, the disclosure provides a method for classification of a biological tissue using a computing system in accordance with claim 1, a computer program in line with claim 27 and computing system as defined by claim 28. Further features are detailed in the dependent claims and herein.

Image data comprising a plurality of images of an examination area of a biological tissue (particularly a cervix of a subject) is received at a computing system. Each image is captured at different times during a period in which topical application of a pathology differentiating agent to the examination area of the tissue causes transient optical effects. In particular, the pathology differentiating agent may comprise acetic acid (typically dilute acetic acid, usually to 3-5%), such that the transient optical effects may comprise an aceto-whitening effect (although other differentiating agents and/or optical effects may be possible, for instance using molecular diagnostics). The examination area may be exposed to optical radiation, which may be broadband (across the majority or all of the optical spectrum) or narrowband (limited to a one or a range of specific wavelengths defining only one or a limited range of colours, possibly including ultraviolet and/or infrared), during the period of image capture. The images captured subsequent to application of the agent (for example, at predetermined and/or regular intervals) may therefore show progress of the transient optical effects. The received image data (which may have been subject to image processing, as discussed below) is provided as an input to a machine learning algorithm (operative on the computing system). The machine learning algorithm allocates one of a plurality of classifications to the tissue. The cervix may also be segmented, for example based on the application of one or more masks (for instance, defined by recognition of morphology or feature extraction) and/or on the basis of local classifications applied across the tissue. Thus, the tissue may be classified into discrete and defined sub-areas of the examination area of the tissue, in particular with a different classification allocated to each segment of the cervix. The classifications may be defined by a scale of values on a continuous range (such as from 0 to 1 or 0 to 100) or a set of discrete options, which might include a plurality of disease tags (for example: negative vs positive or for example: low risk; medium risk; high risk, specific disease states, for instance: CIN1, CIN2, CIN3, or the presence of one or more characteristics of morphology, such as presence of atypical vessels, sharp lesion borders or disease, such as persistent or dense aceto-whitening).

In the approach disclosed herein, automatic in vivo or in vitro classification of the biological tissue may be achieved. The use of multiple images taken over the progress of the transient optical effects may have a significant improvement on sensitivity and/or specificity of the classification over existing methods. Sensitivity and specificity may refer to the ability to identify cervical dysplasia and/or cervical neoplasia. Sensitivity thus refers to the ability to correctly identify tissues displaying cervical dysplasia and/or cervical neoplasia. Specificity thus refers to the ability to correctly identify tissues that do not display cervical dysplasia and/or cervical neoplasia. Depending upon the application context, the output may be focussed on maximising sensitivity or specificity, or operating at a threshold that may optimal for one or both. Although classification may be presented based on the subject/tissue as a whole, the invention permits regions of the tissue suspected to be precancerous or cancerous to be identified. This may be advantageous for directing biopsy or treatment, including surgical resection. These sites may be biopsied to confirm the identification. A successful implementation of such a system may render the taking of biopsy unusual in many or most cases. For example, a patient may be directly directed for discharge to routine screening or for treatment, based on the output of such a classification. Moreover, the output of the machine learning algorithm may be more clinically useful than for existing approaches, as will be discussed below. The technique may be implemented as a method, a computer program, programmable hardware, a computer system and/or in a system for tissue examination (such as a colposcopy system).

For example, a computing system operative for classification of a tissue may comprise: an input for receiving the image data; and a processor for operating the machine learning algorithm. In embodiments, it further comprises an image collection module for capturing optical images (for example, raw images) from which the image data is based. The image collection module may be located remotely from the processor. In some designs, the processor comprises a plurality of processing devices, each operating a part of the machine learning algorithm (for example in a distributed way). Then, the image collection module may be located remotely from at least one of the processing devices. Approaches applicable to any of the possible implementations in accordance with the disclosure (whether as method or program steps and/or as structural features) are discussed below.

The image data provided as an input to the machine learning algorithm may be derived from captured optical images, that is raw images, taken by an image collection module (which may form part of the computer system or it may be external). For example, the optical (raw) images may be scaled (for instance based on a focusing distance for the respective optical image). This may allow the plurality of images for one tissue to have the same scale as for another tissue. Each of the images may have the same pixel arrangement (that is, the same image size and shape). Alignment of the plurality of images may be achieved by applying one or more transformations to the optical images. Artefacts may be removed from the optical images by image analysis and/or processing. The images may be broken down or sub-divided into patches (for instance, a contiguous block of pixels, preferably two-dimensional), which may form the image data. The patches may be overlapping, for example patches created at a stride smaller than the patch size, which may increase resolution.

An additional input to the machine learning algorithm may be based on processing of each of the plurality of images to extract tailored features, based on mathematical functions describing local colour, gradient and texture, although other characteristics may also be envisioned. This may be done separately on sub-portions of the image defined as patches of a block of pixels (for example, a square block of 8×8, 16×16, 32×32 pixels or other sizes, a rectangular block or another shape of block). Each image may be broken down to a number of patches with a stride between them, which can be at 4, 8, 16, 32 pixels (with other sizes also possible). As noted above, the patches may be provided as the image data provided as an input to the machine learning algorithm.

Map data comprising a respective analysis index for each pixel may be obtained at the computer system. The analysis indices are derived from the plurality of images, for example based on one or more of: a maximum intensity for the pixel over the plurality of images; a time to reach the maximum intensity for the pixel; and a summation of an intensity for the pixel over the plurality of images (which may include a weighted summation, for example to provide an area under a curve of intensity against time of image capture). Each of these parameters may be limited to a predetermined spectral bandwidth and/or multiple such parameters (of the same or different type) may be used each for different spectral bandwidths. The data for the same pixel across multiple images may be fitted to a curve and this curve may be used to obtain the parameter. This gives rise to useful parameters selected from one or more of: the area under the curve (integral), the area under the curve up to the maximum intensity ("area to max"), the (fitted or average) slope of the curve up to the maximum intensity, the (fitted or average) slope of the curve after the maximum intensity. Specific parameters useful in the present invention are discussed in WO2008/001037, incorporated herein by reference in its entirety. A weighted combination of multiple parameters (of different types and/or for different spectral bandwidths) may be used to establish the analysis indices. The analysis indices may represent a measure of diffuse reflectance. Advantageously, the map data may be provided as a further input to the machine learning algorithm, for example as a further image input.

The machine learning algorithm advantageously comprises a neural network and more preferably a deep neural network (comprising more than one hidden layer), although implementations using a shallow neural network may be considered. The deep neural network optionally comprises one or more of: a convolutional neural network; a fully-connected neural network; and a recurrent neural network, but other types of networks may also be considered. The deep neural network may comprise one or more convolutional neural network layers. The machine learning algorithm is preferably multi-modal, in that it can receive image and non-image data as inputs for training and testing.

In embodiments, the images are processed to identify and/or quantify one or more extracted features and/or at least one morphological characteristic, such as one or more of:

atypical vessels; mosaicism; and punctation. The one or more extracted features and/or at least one morphological characteristic may be provided as an additional input to the machine learning algorithm. In a less preferred approach, this may allow division of the images into patches (based on the one or more extracted features and/or at least one morphological characteristic).

One or more subject characteristics (each relating to a subject from which the biological tissue originates) may be provided as another input to the machine learning algorithm. For example, the subject characteristics may comprise: subject risk factors and/or subject clinical test results. Subject risk factors may include one or more of: an age of the subject; a smoker status of the subject; status of vaccination against HPV; number of sexual partners; condom use; and a parity for the subject. Subject clinical test results may comprise one or more of: a prior cytology result; a prior human papillomavirus (HPV) test result; a prior HPV typing test result; a prior cervical treatment information; and a prior history of screening for cervical cancers or pre-cancers.

Beneficially, the machine learning algorithm allocates one of a plurality of classifications to each of one or more segments of the tissue. The segment or segments may be identified from the image data using the machine learning algorithm, for example to identify individual regions of interest or lesions. A portion of the images corresponding with the cervix may be identified in some embodiments, which may allow suitable segments to be determined. For example, the classifications may take the form of diagnostic tags. In another option, the classifications may be in the form of a 'heat map' of an image of the tissue (that is an output image, advantageously based on the plurality of images), in which the intensity and/or colour of each pixel is indicative of a classification for that pixel, preferably a probabilistic classification for the pixel. In another option the classification output may be in the form of a risk tag, whereby a tissue area is highlighted (for example by a bounding box) as no, low or high risk. Optionally, an overall classification for the tissue may also be allocated. This may be based on the classifications allocated to the segments or the result of a (separate) parallel machine learning model.

The machine learning algorithm is advantageously trained based on a respective plurality of images and a respective allocated classification (or classifications, if applicable) for each of a plurality of other biological tissues. The number of other biological tissues may be large, for instance at least 500, 1000, 2000 or 5000. The allocated classification may be such as that a specific region (or group of multiple regions) of each tissue is characterized by histopathology readings.

The machine learning algorithm may also be continually and/or dynamically trained (incremental learning) using methods such as transfer learning and selective re-training (such as described in "Lifelong Learning with Dynamically Expandable Networks", Yoon et al, ICLR 2018), by providing a user-determined or database classification for the tissue (such as provided by a medical professional, for example from biopsy or excisional treatment with histology or subjective assessment) to the machine learning algorithm (and/or a version of the machine learning algorithm operative on a second computer system). Where the machine learning algorithm is provided in a distributed way, a first part may be provided local to the image collection module and a second part may be provided more remotely. Both parts may be capable of allocating classifications. The continual (dynamic) training may be applied only to the second part, particularly in batches and may incorporate data from multiple different first parts. The first part may be a fixed algorithm, which may be updated (at intervals, for instance after a plurality of classifications or a specific length of time).

BRIEF DESCRIPTION OF THE DRAWINGS

The invention may be put into practice in a number of ways and preferred embodiments will now be described by way of example only and with reference to the accompanying drawings, in which.

DETAILED DESCRIPTION OF PREFERRED EMBODIMENTS

Figure 1:
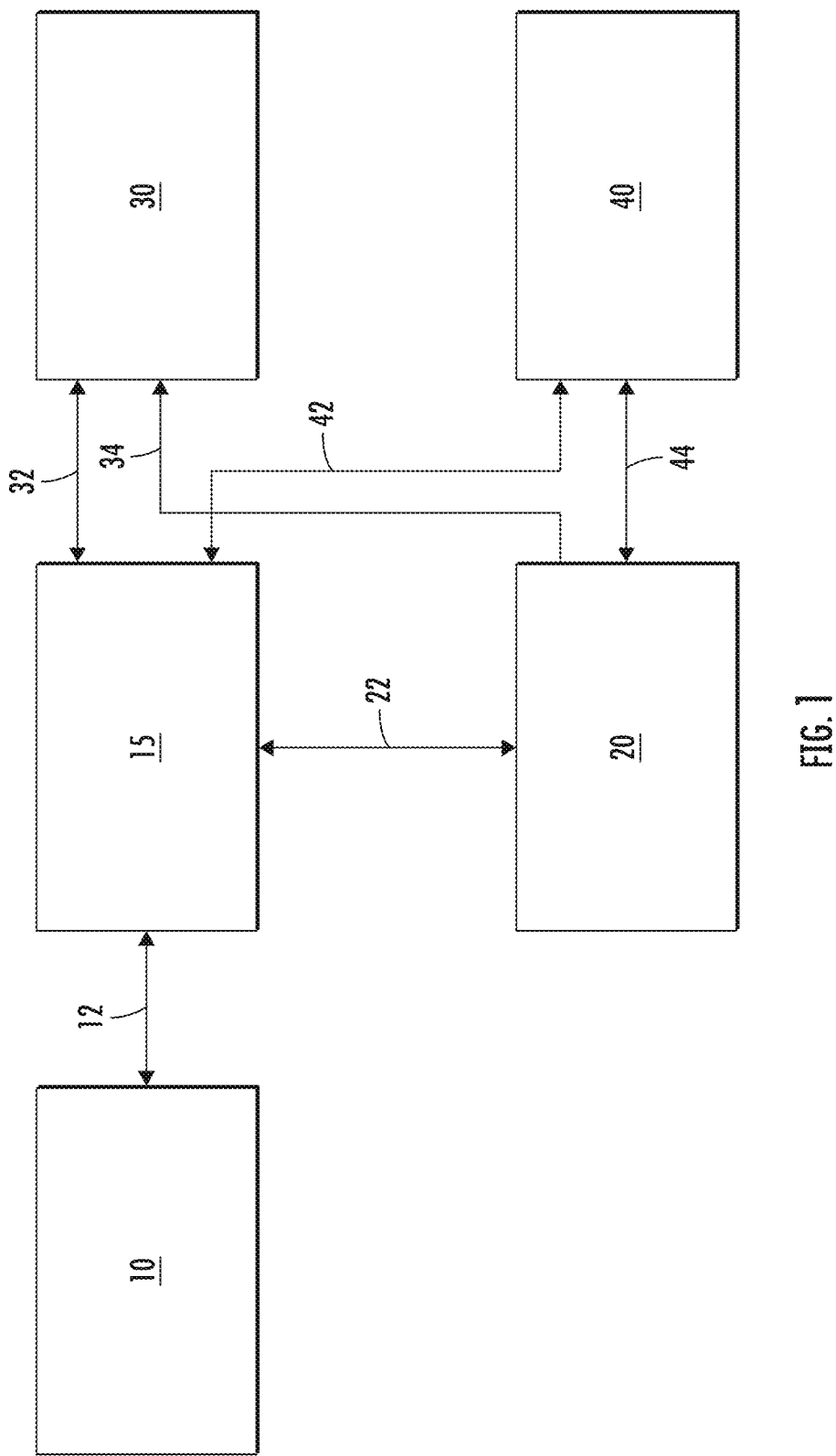
FIG. 1 shows a schematic diagram of a computing system in accordance with the disclosure.

Referring first to FIG. 1, there is shown a schematic diagram of a computing system in accordance with the disclosure. The computing system comprises: an image collection module 10; a local processor 15; a main server 20; an identity database 30; an imaging database 40. A local interface 12 couples the image collection module 10 with the local processor 15. A processing interface 22 couples the local processor 15 with the main server 20. A first identity interface 32 couples the identity database 30 with the local processor 15 and a second identity interface 34 couples the identity database 30 with the main server 20. A first image data interface 42 couples the imaging database 40 with the local processor 15 and a second image data interface 44 couples the imaging database 40 with the main server 20. It will be noted that the computing system of FIG. 1 incorporates parts that may be distinct from a computer, for example being part of an optical system and/or an electronics control system. However, these will all be considered part of the computing system for the purposes of this disclosure.

The image collection module 10 is a colposcopic imaging unit, for capturing and collection of optical images of an examination area, in particular a cervix uteri. Although the main embodiment of the present invention relates to a colposcopic system and there are significant and distinct advantages applicable to such a system, it will be understood that the implementation described herein may be used for other types of system for examination and/or imaging of biological tissue. The image collection module 10 is controlled by the local processor 15, which may include a user interface, for example comprising controls and/or display. The identity database 30 is used to store patient identity data. During an examination, the local processor may interface with the identity database 30 using the first identity interface 32, to retrieve identity data for the patient being examined. Images collected during the examination are stored in the imaging database 40 via the first image data interface 42. A patient identifier may be stored with the patent images to allow cross-referencing with the information stored in the identity database 30.

As part of the examination process, dilute acetic acid is topically applied to the cervix, which causes an aceto-whitening effect. Images of the cervix are taken during the process of aceto-whitening. Initiation of the capture of images occurs after the application of the dilute acetic acid and may further occur before and at the time of the application (to provide a reference image). The target or examination area, including the cervix, is illuminated. The properties of the illumination are typically standardized and quantified in terms of beam characteristics, colour profile and intensity. The series of optical images of the cervix are captured over time for the purpose of quantifying any changes in the optical properties of the cervical epithelium. Typically, the images are taken at predetermined times relative to the time at which the dilute acetic acid is applied. The predetermined times may be at regular intervals or there may more frequent at first and less frequent subsequently. These images are stored in the imaging database 40, as discussed above. The images may be captured and/or stored in the form of discrete images and/or as a video format or stream and optionally are also displayed using the user interface of the local processor 15 (having one or more screens), which may allow the operator to also perform an examination. The image collection module is calibrated, so that it has standardized and measurable characteristics (such as field of view and/or colour profile and/or response to light intensity). The focusing distance for each image is known and saved. The optical images may capture a broad frequency spectrum or a narrow frequency spectrum (for example, limited to one or more specific optical frequency bands, each of which is smaller than the full optical spectrum, such as specific colours or groups of colours).

Processing of the 'raw' optical images (the term "optical images" herein typically refers to raw images or such images prior to completion of image processing and/or analysis) may take place at the local processor 15 and/or at the main server 20, for example in the form of an image analysis sub-system. One form of processing is standardising the size of the images. For a fixed focal length optical system, this may be achieved with reference to the focusing distance for each optical image. Typically, the focusing distance for each of the optical images of the same examination area will be the same (especially when using a colposcopic apparatus as described in International Patent Publication number WO-01/72214, in which the relative position between tissue and optical head of the apparatus remains almost constant during the capture of multiple images. Using the respective focusing distance for the optical image, the image can be scaled to a standard size (so that each pixel corresponds to a standard physical length). This allows comparison of images taken for different tissues. However, if a less advantageous colposcopic apparatus is used, in which the relative position between tissue and optical head of the apparatus may vary, the plurality of images may each be scaled to standardise their size.

A typical resolution for sizing the images is 1024×768 or 2048×1536, but other resolutions are possible. Another form of processing is alignment of the images with reference to a specific feature shown in the image, such as the cervix. The aim of such alignment is to compensate for natural movements such as displacements and contractions during capture of the optical images. Such alignment may be effected by identification of one or more specific features in each of the images and comparison of the images based on the feature identification, to determine transformation parameters (such as for translation, rotation, magnification or deformation) to achieve alignment of the features through the image stack. Standard image processing techniques can then be used to implement transformations based on the determined transformation parameters. A further form of image processing may include an algorithm to process the raw optical images or post-processed images, to identify the area of the cervix against background (region of interest). Artefacts that may coexist on the images, such as reflections may be identified and removed, in another form of processing. Pattern recognition may further identify morphological characteristics, such as one or more of: atypical vessels; mosaicism; and punctation. Typically, all forms of image processing technique are used, but only a subset may be applied in some embodiments. Moreover, different forms of processing may be performed in different parts of the system. Processed images are in high-quality JPEG or PNG format and in RGB colour mode (but different formats may be accepted). Quality metrics may be used to allow identification of issues with the images, such as areas that exhibit glare or other artefacts and unfocused images. This may allow their exclusion from any analysis and/or providing feedback to users.

In recent years, Artificial Intelligence (AI) has emerged as a proven method to be implemented in a range of human activity areas, including medical and health-related applications. Advanced algorithms developed across the scientific community promise more accurate and efficient processes. The application of AI for processing medical images, particularly using an image of a cervix to which the aceto-whitening process has been applied, has already been considered. It has now been recognised that the application (for instance collection and analysis) of multiple images of the cervix during the aceto-whitening process may significantly improve the performance of the AI. This may be because of a surprising recognition that in transient optical effects, such as the aceto-whitening effect, the effect may be different not only at the end of the process, but also during the process itself. Observing only one instant of the process provides some information about the biological tissue, specifically the cervix in this case. However, as the process may not be uniform across the cervix, observing the whole process may provide significant additional information, which may be especially useful in correctly classifying the optical effects and their meaning for the biological tissue. The AI provided with multiple images of the process may thereby permit a colposcopic method to identify and/or characterize areas suspicious for cervical neoplasia.

The AI in the system of FIG. 1 is provided in both the local processor 15 and the main server 20. Both systems are able to access the plurality of images of the cervix captured during the aceto-whitening process and stored in imaging database 40. The local processor uses a fixed AI algorithm, which allows immediate classification of the cervix based on the images. The main server 20 uses an AI algorithm that is updated more regularly, preferably in batches of results (in other words, the algorithm is continuously and dynamically learning from the batches of data) and, less preferably, may be updated with each new examination. To effect this, the AI algorithm in the main server 20 may have a different structure and/or parameterisation in comparison with the fixed AI and this difference may increase over time as further training is provided to the AI algorithm in the main server 20. The local processor 15 uses a fixed AI algorithm, which may be updated at intervals, preferably using the AI algorithm trained in the main server, in particular once it has developed to a steady state. The fixed AI algorithm may provide faster results than the AI algorithm operative on the main server 20. The main server 20 may be cloud-based, so that is able to collect and analyse cervical image datasets from multiple remote devices. The training set may therefore be large and able to capture differences resulting from demographic changes or changes in the screening programmes, for example.

The AI may be implemented at the local processor 15 and/or main server 20 as a software module. This AI comprises a machine learning algorithm. Typically, this uses neural networks and may be a deep neural network (which comprises more than one hidden layer). More specifically, a fully-connected neural network (fcNN), a recurrent neural network (RNN) or a convolutional neural network (CNN), or combinations of these or other types of neural networks in ensemble schemes may be used. In the most basic embodiment, the AI is provided with the data from multiple images captured during the aceto-whitening effect, as will be discussed below. However, additional data is preferably also provided to the AI. In that case, the AI may comprise a multi-modal neural network, which may combine image and non-image data.

The images provided to the AI can be the time series of 'raw' images as captured by the optical system. However, the images will more typically be provided post-processing of the 'raw' optical images, especially following scaling and/or alignment by the software algorithm and/or after processing for one or more of: cervix identification; artefact removal; and pattern recognition. Both raw and post-processed images could be provided as inputs in some implementations. The entire set of images as captured or a subset of the image set (in either case, with or without further processing) may be provided as the input to the AI. For example, the raw or post-processed images may be sub-divided into patches, which may be provided as the image data. The patch sizes and/or number of patches provided may vary between images. Feature extraction and/or other processing described herein may be applied to the patches, rather than the overall or whole image.

One additional input to the AI may be based on further data processing of image data (typically post-processing of the 'raw' optical images, especially to achieve the same scaling and alignment). This further data processing may be used to measure diffuse reflectance characteristics in the images and may be carried out at the local processor 15 and/or main server 20. Initially, pixel values (such as intensities) may be extracted from the aligned images and referenced according to the time at which the image was captured (which may be absolute time or relative to the time at which the dilute acetic acid was topically applied). Different parameters are then calculated from the time-resolved pixel values, such as the maximum intensity, the time-to-maximum intensity and the area under a curve of the pixel value against time (that is, an integral of the pixel value over time). These parameters may be calculated in one or multiple spectral bands and/or for all or a sub-sample of the image pixels. Although the parameters may be based directly on the time-resolved pixel values as captured, the parameters may instead be calculated using intermediate values calculated from the time-resolved pixel values. For example, the intermediate values may be determined by fitting the extracted time-resolved pixel values to a mathematical function (such as a linear function, a curve or an exponential). Then, the coefficients of this function can be used to calculate the different parameters, such as the maximum intensity, the time-to-maximum intensity and the area under the pixel value against time curve. Such parameters may be used as specific inputs to the AI, which may be representative of the level of diffuse reflectance. In another approach, the parameters may be used to calculate a single numerical index value per pixel, for instance from a single parameter or from a weighted combination of the parameters. The single numerical index value per pixel may then be provided as an input to the AI. Alternatively, a colour from a pseudo-colour scale may be assigned to each pixel based on its index value and a parametric pseudo-colour map may be produced by plotting the corresponding pseudo-colour over each pixel of the cervical image. Then, this parametric pseudo-colour map may be provided as an input to the AI.

One additional input to the AI may be based on further data processing of image data (typically post-processing of the 'raw' optical images, especially to achieve the same scaling and alignment). This may be done separately on sub-portions of the image that may be defined as patches of 8×8 or 16×16 or 32×32 pixels (with other shapes and/or sizes of patches also possible). Each image may be broken down to a number of patches with a stride between them, which may be at 4, 8, 16, 32 pixels (with other sizes also possible). In this way each patch may have partial overlap with its neighbouring patches and a large number of patches can be extracted from each image or portion of image. This further data processing may be used to extract tailored or hand-crafted features, based on mathematical functions describing local colour, gradient and texture (with other types of functions also possible). Then, these features may be provided as an input to the AI.

Other forms of information may be provided as one or more additional inputs to the AI, for example using information stored in the identity database 30. Such information may include one or more of: patient demographics; patient risk factors; previous medical history information; and clinical test results. Patient demographics may comprise, for example, the age of the patient at the time of the examination (or that the age is above a predefined threshold). Patient risk factors may include: a smoker status for the patient (such as one of no-smoker, regular smoker, casual or has been smoker); a sexual status and/or history for the patient; the use of condoms during intercourse (such as one of always, occasionally or never); the status of vaccination against HPV; and a parity for the patient (in terms of whether there has been any birth and/or the number of births). The patient clinical test results may comprise at least one or any combination of: prior cytology results; prior HPV test results; prior HPV typing test results; prior cervical treatment information; and prior history of screening for and/or diagnosis of cervical cancers or pre-cancers. The possible cytology results may be one of (ordered by severity): Normal, ASCUS (borderline), LSIL (mild dyskaryosis), ASC-H, moderate dyskaryosis, severe dyskaryosis (HSIL), suspected glandular changes or suspected invasive cancer. The possible results for the HPV tests may be one of Negative, HR-positive, 16 positive, 16/18 positive or other.

In general terms, there may therefore be considered a method for (in vivo or in vitro) classification of a biological tissue, such as a cervix uteri, using a computing system. Image data, comprising a plurality of images of an examination area of a biological tissue, is received at the computing system. Each of the plurality of images is captured at different times during a period in which topical application of a pathology differentiating agent (particularly comprising acetic acid, which is preferably diluted) to the examination area of the tissue. This causes transient optical effects, such as whitening, which may be aceto-whitening (where acetic acid is employed). The received image data is provided as an input to a machine learning algorithm operative on the computing system (specifically one or more processors of the computing system, for instance). The machine learning algorithm, which advantageously comprises a neural network and more preferably a deep neural network, is configured to allocate one of a plurality of classifications to the tissue. In the preferred embodiment, the machine learning algorithm is configured to allocate one of a plurality of classifications to each of a plurality of segments of the tissue, which advantageously may be presented in the form of a heat-map indicating the classifications (as will be discussed further below). The method may be implemented as a computer program.

In another sense, there may be considered a computing system operative for classification of a tissue, comprising: an input configured to receive image data comprising a plurality of images of an examination area of a biological tissue; and a processor, configured to operate a machine learning algorithm configured to allocate one of a plurality of classifications to the tissue based on the image data. Each of the plurality of images is captured at different times during a period in which topical application of a pathology differentiating agent to the examination area of the tissue causes transient optical effects.

Before providing further implementation details of the preferred specific embodiment, some optional and/or advantageous features of this generalised method and/or computer system will be discussed. Such features may typically be applied to either aspect.

The plurality of images (or optical images from which the plurality of images are derived, also termed raw images) are generally captured at intervals (which may be regular, but need not be so) of a predetermined duration, during the period in which the topical application of a pathology differentiating agent to the examination area of the tissue causes the transient optical effects. At least one image of the biological tissue prior to the topical application of the pathology differentiating agent to the examination area of the tissue causing transient optical effects may be captured (a baseline reference image) and this may be provided as a further input to the machine learning algorithm. The examination area is advantageously exposed to broadband optical radiation during the period in which topical application of a pathology differentiating agent to the examination area of the tissue causes transient optical effects. The broadband optical radiation preferably has a bandwidth based on the transient optical effects, for example of a bandwidth that will cause an aceto-whitening effect to be visible in the captured images. The level of illumination of image brightness achieved by the optical radiation may be well-characterized with respect to incident light intensity and distance between light source and target. The broadband optical radiation may cover the whole optical spectrum, at least 90%, 80%, 75%, 70%, 60% or the majority (50%) of the optical spectrum. Narrowband optical radiation may be used in some cases, for example for certain pathology differentiating agents (such as molecular diagnostics, for instance using fluorescein markers). In that case, the narrowband optical radiation may cover less than 50%, 40%, 30%, 20% or 10% of the optical spectrum, for instance limited to a single colour, such as ultraviolet or infrared.

The processor of the computing system may comprise a single processing device or a plurality of processing devices. Each processing device is optionally configured to operate a part of the machine learning algorithm (for example, in a distributed way). The processing devices may be located in different (remote) locations.

A plurality of optical images (raw images) of the examination area of the biological tissue are advantageously captured. This may be achieved using an image collection module (comprising a suitably mounted camera and/or under control of the processor). The image collection module is optionally located remotely from the processor on which the machine learning algorithm is operated (or at least one of processing devices, where multiple processing devices are used).

The plurality of images of the image data may be derived from the plurality of optical (raw) images. Optionally, one or more of the plurality of optical images is provided as an additional input to a machine learning algorithm. Beneficially, the image collection module is calibrated, for example at regular intervals or after a predetermined number of image captures and/or examinations of individual biological tissues (or patients). Each optical image may be captured at a respective focusing distance. The focusing distances may be the same. The optical image may then be scaled based on the focusing distance and a reference distance to provide a respective one of the plurality of images, in particular such that the scale of each of the plurality of images is at a predetermined level. Each optical image is preferably transformed so as to provide alignment of the examination area within the plurality of images. Additionally or alternatively, each optical image may be processed to remove one or more artefacts or types of artefacts. The plurality of images may be processed to identify a portion of the plurality of images corresponding with a predetermined organ. For example, where the biological tissue comprises a cervix, the plurality of images may be processed to identify a portion of the plurality of images corresponding with the cervix. In some embodiments, the plurality of images may be processed to identify and/or quantify at least one extracted feature and/or at least one morphological characteristic, such as one or more of: atypical vessels; mosaicism; and punctation. The extracted feature or features and/or the morphological characteristic or characteristics may be provided as an additional input (or additional inputs) to the machine learning algorithm.

Each of plurality of images is defined by a respective set of pixels and optionally, each of the sets of pixels has the same pixel arrangement. In the preferred embodiment, map data is obtained, comprising a respective analysis index for each pixel of the pixel arrangement, the analysis indices being derived from the plurality of images. Preferably, the analysis index for a pixel is generated based on at least one parameter derived from the plurality of images. The at least one parameter is optionally limited to a predetermined spectral bandwidth and where multiple parameters are derived, these may comprise a first parameter limited to a first predetermined spectral bandwidth and a second parameter of limited to a second predetermined spectral bandwidth (different from the first predetermined spectral bandwidth). Each parameter may be determined based on the exact data of the pixel and/or by fitting data for the pixel across the plurality of images to a line or curve and determining the parameter from the curve. The analysis index for each pixel may be based on a single parameter or a weighted combination of multiple parameters. The at least one parameter comprises, for example, one or more of: a maximum intensity for the pixel over the plurality of images; a time to reach the maximum intensity for the pixel; and a summation or weighted summation of an intensity for the pixel over the plurality of images. The weighted summation of an intensity for the pixel over the plurality of images may use weights based of the time of capture for each of the plurality of images, for example their relative time of capture. This may allow an integration of the intensity over time to be calculated (or an area under a curve of intensity against time). The map data (or at least one or more of the analysis indices) may be provided as an additional input to the machine learning algorithm.

In some embodiments, one or more subject characteristics are provided as an input to the machine learning algorithm. Each subject characteristic may relate to a subject from which the biological tissue originates. For example, the one or more subject characteristics may comprise one or more of: subject risk factors (such as one or more of: an age of the subject; a smoker status of the subject; the HPV vaccination status of the subject; the use of condoms during intercourse; and a parity for the subject); and subject clinical test results (for example, one or more of: a prior cytology result; a prior HPV test result; a prior HPV typing test result; a prior cervical treatment information; and a prior history of screening for and/or diagnosis of cervical cancers or pre-cancers).

Figure 2:
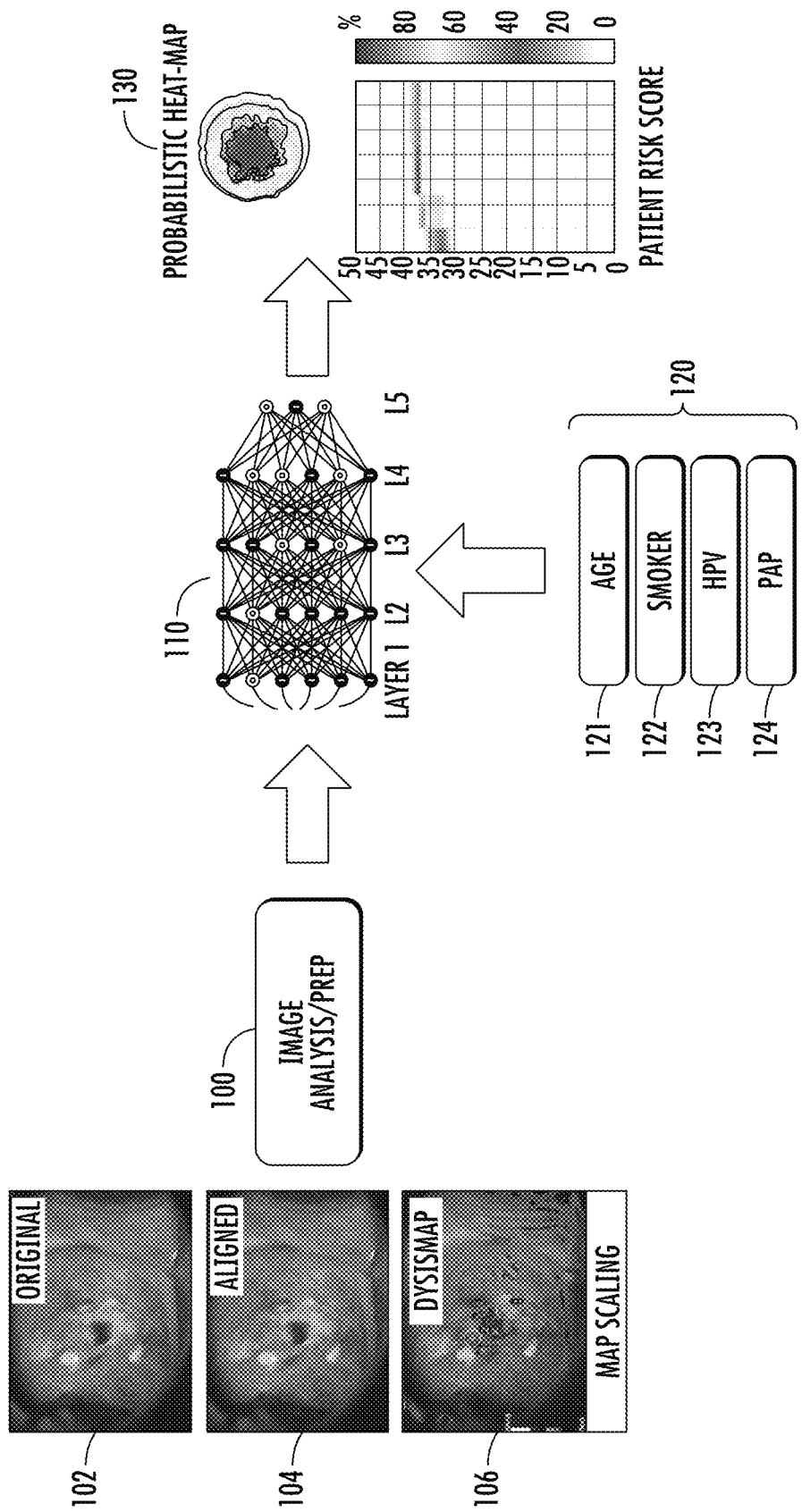
FIG. 2 schematically depicts a process in accordance with the disclosure.

Further implementation details will now be discussed. Referring now to FIG. 2, there is schematically depicted a colposcopic analysis process in accordance with the disclosure. As shown on the left hand side of the depiction, the initial step in the process is the capturing, preparation and analysis of images 100. Initially, original images 102 are captured, these are then processed to produce aligned images 104 and a parametric pseudo-colour map 106 is produced. These are provided as inputs to an AI processing step 110. Also provided as an input to the AI processing step 110 is non-image data 120, which may include: age information 121; smoker status 122; HPV status 123; and Pap test status 124. Different and/or additional inputs are also possible, as discussed herein.

The AI (particularly the algorithm operative on the main server 20) is trained to classify the tissue from which the images were captured in some sense. Different datasets may be used to train different aspects of the AI. The type or types of data used for training may typically include any one or more of the type or types of data used for classification. In one implementation, the AI is configured to give a Cervical Intraepithelial Neoplasia (CIN) classification, based on training data comprising images and a relevant classification from a well characterized set of patient cases with known biopsy areas and histopathology outcomes. In particular, this is a set of cases with known sites that were biopsied and histology outcomes of the biopsies are advantageously known. Expert reviewer annotations of suspicious areas may also be available and these may be provided as further training data. In certain implementations, the set of cases have undergone excisional treatment and a detailed mapping of their histology is available, including multiple sections per treatment specimen, which can also be provided as training data. The AI may classify the cervix on a risk scale, where the different levels of this scale correspond to the patient's overall risk of having different grades of CIN (for example on a scale of 0 to 1, 0 to 100 or 1 to 100 on an integer or continuous scale). Different thresholds on this scale may be selected to fine-tune the final performance or provide a direct indication of no, low or high risk. In another embodiment the AI may directly provide the results in classifications, for example Normal, CIN1, CIN2, CIN3, AIS or Invasive cancer (one of a plurality of disease tags).

Training data sets may be provided from clinical trials. These may include one or more of timed (dynamic) images of the cervix with aceto-whitening (in their original and aligned form), the constituent data to provide a parametric pseudo-colour map for the images, histology results (with biopsy locations where known), as well as patient baseline characteristics (age, cytology, HPV, smoker status, previous history of disease or others). A patient dataset may include the set of images as captured during the examination with a reference image (pre-acetic acid application) and all subsequent (post-acetic acid) timed images (up to 24). The image resolution may be 1024×768, 1600×1200 or 2800×2100, with other resolutions also possible. Additionally or alternatively, the patient dataset may include the set of images as aligned by the image processing algorithm, which may contain a reference image (pre-acetic acid application) and all subsequent (post-acetic acid) timed images (up to 24). The aligned image resolution may be 1024×768 or 2048×1536, for instance. A typical resolution for the parametric pseudo-colour map is 1024×768 or 2048×1536, for example. Histology results can be one of (ordered by severity): Normal, CIN1, CIN2, CIN3, AIS, Invasive cancer.

Although a single classification for the tissue may be output from the AI, other options are also possible. In a specific implementation, the AI analyses and may segment the image of the cervix for each patient examined with the system. The image may be segmented in a predetermined way or based on the identification of lesions or disease risk and optionally may be done outside the machine learning algorithm. Each segment of the cervix is then classified on a risk scale for the estimated risk for different grades of CIN (as discussed above) or to provide a classification from one of a number of discrete disease states. Optionally, the AI may also classify each pixel and/or segment in accordance with a determined presence of a morphological characteristic. This may be an intermediate output of the AI, which may be used to determine further classifications but need not be provided as an output to a user.

The AI segmentation and classification results may be displayed as a probabilistic "heat-map" (a parametric pseudo-colour map), as an output of the AI. This is shown as an AI output 130 in FIG. 2. The heat-map output from the AI (which is different from the parametric pseudo-colour map produced by processing the images as described above and which may be used as an input to the AI) is then advantageously displayed in a graphic form as an overlay on the cervical images to the system operator during the examination (for instance via the local processor 15) to facilitate reading and clinical decisions. The resolution of the heat-map may be the same as the scaled images provided as input to the AI (such as 1024×768 or 2048×1536, for instance). This (or similar image processing) may allow overlaying of the AI heat-map output on an image of the cervix captured during examination (for instance, post-processing). Such a "heat-map" may be of significant clinical utility (such as for biopsy site identification or excisional treatment).

The AI segmentation and classification results may alternatively be displayed as a bounding box that indicates areas that achieve a classification score above a pre-defined threshold as an output of the AI. For example this may be as indication of no, low or high risk, or directly with a disease tag, for instance: Normal; CIN1; CIN2; CIN3; AIS; or Invasive cancer.

For each outcome it produces, the AI module may also calculate an accompanying confidence interval or another measure of accuracy that can be in graphical or numerical form.

The approach discussed in this disclosure will improve the accuracy and the receiver operating characteristic (ROC) curve performance. This may be measured as the AUC ("Area Under Curve"), which, because the ROC curve plots the true positive rate against the false positive rate and thus depicts the combined performance of sensitivity and specificity. The performance of the AI can be determined by comparing the AI classification to ground truth (histology result) for each tested patient and characterised the comparison as one of: true positive (TP); false positive (FP); true negative (TN); and false negative (FN). Main metrics for comparison may be the overall accuracy, sensitivity and specificity. Secondary measures may include the positive and negative predictive values.

With reference to the general sense discussed above, it may be considered in some embodiments that the machine learning algorithm is configured to allocate one of the plurality of classifications to each of one or more segments of the tissue. The one or more segments of the tissue are optionally identified from the image data, for example using the machine learning algorithm. Alternatively, the segments may be based on a number of pixels in each image of the image data. An output image may be generated (and optionally displayed), showing the examination area of the biological tissue based on the image data and indicating the classification allocated to each of the plurality of segments of the tissue. For instance, this may take the form of a heat-map. Thus, the plurality of segments of the tissue can represent sub-areas of the examination area of the biological tissue. Those sub-areas may be defined and delineated from other sub-areas on the basis of one or more masks, feature extraction and/or a common classification allocated to a particular sub-area. This means that the shape and size of the sub-areas may in this case be determined by the features and/or classifications applied across the tissue (and therefore may not be uniform in size or shape). Accordingly, improved performance may be measured on the basis of the ability to apply individual classifications to the different portions of the tissue (as opposed to an overall tissue classification).

A classification may be allocated to the (entire or overall) tissue based on the classification allocated to the one or more segments of the tissue (or from a combination of classifications allocated to multiple segments, such as a weighted sum). Additionally or alternatively, the classification allocated to the (entire or overall) tissue may be based on an algorithm different from the machine learning algorithm, for example a different, parallel model. The classifications may be discrete or defined by a scale of values on a continuous range (for example, as a probability, risk level or score, such as of a certain condition being present).

The machine learning algorithm (or a version operative on a second computer system, which may be remote from the computer system) may be trained based on a respective plurality of images and a respective allocated classification for each of a plurality of other biological tissues (which may be captured at different times during a period in which topical application of a pathology differentiating agent to the examination area of the tissue causes transient optical effects). The number of other biological tissues may be at least 100, 500, 1000 or 5000 in some cases. Optionally, a user-determined or database classification for the tissue may be provided to the machine learning algorithm for its further training. This may be based on one or both of a biopsy with known histology outcome or the clinical assessment of a highly trained medical professional. Such classifications may be manually provided (for example directly by a clinician, medical professional or technical) and/or they may be automatically pulled from a database, for example of the patient records, which may form part of an input dataset. The classifications may then have been input to the database (or a different database, from which the dataset was partly or fully derived) manually.

In some embodiments, a classification may be allocated to the tissue using a first machine learning algorithm operative at a first processor of the computing system. In some cases, the first processor is local to an image collection module, which is being used to capture a plurality of optical (raw) images of the examination area of the biological tissue, from which the plurality of images are derived. Optionally, a classification may also be allocated to the tissue using a second (different) machine learning algorithm, operative at a second processor of the computing system. Additionally or alternatively, the second machine learning algorithm (described above as a version of the machine learning algorithm) may be trained, for instance using the classification or classifications identified by the first machine learning algorithm. The second processor is preferably remote from the image collection module and in certain cases, the first processor may also be remote. The second machine learning algorithm advantageously has a different structure and/or parameterisation in comparison with the first machine learning algorithm. In some embodiments, the classification allocated at the first processor may be provided as an input to the second processor.

In an embodiment, the second machine learning algorithm may be trained by providing a user-determined or database classification for the tissue to the second machine learning algorithm (for instance from a biopsy with known histology, as discussed above). However, the first machine learning algorithm is optionally not trained by providing a user-determined or database classification for the tissue to the first machine learning algorithm. In this way, a (quick and/or lower complexity) machine learning algorithm may be provided without training (that is, a fixed algorithm), with a (slower and/or more sophisticated) machine learning algorithm provided with continuous dynamic training (incremental learning), for instance based on additional data being provided. In accordance with continuous dynamic training for example, the second machine learning algorithm may be provided with, for each of a plurality of examination areas of one or more biological tissues one or more of: a plurality of images of the examination area (as provided to a machine learning algorithm operative on a computer system); one or more biopsy locations (carried out for that examination area); the plurality of classifications to each of a plurality of segments of the tissue allocated by the first machine learning algorithm (operative on the computer system, that is, a local algorithm); and results of histopathology for the tissue. The machine learning algorithm without training may be local to the image capture and/or the machine learning algorithm with continuous dynamic training may be remote to the image capture. The process of continuous dynamic training is advantageously performed in batches. Beneficially, the process may incorporate data from multiple separate image capture devices (each with a respective, local machine learning algorithm). The first machine learning algorithm (the fixed algorithm) may be updated from time to time.

Figure 3:
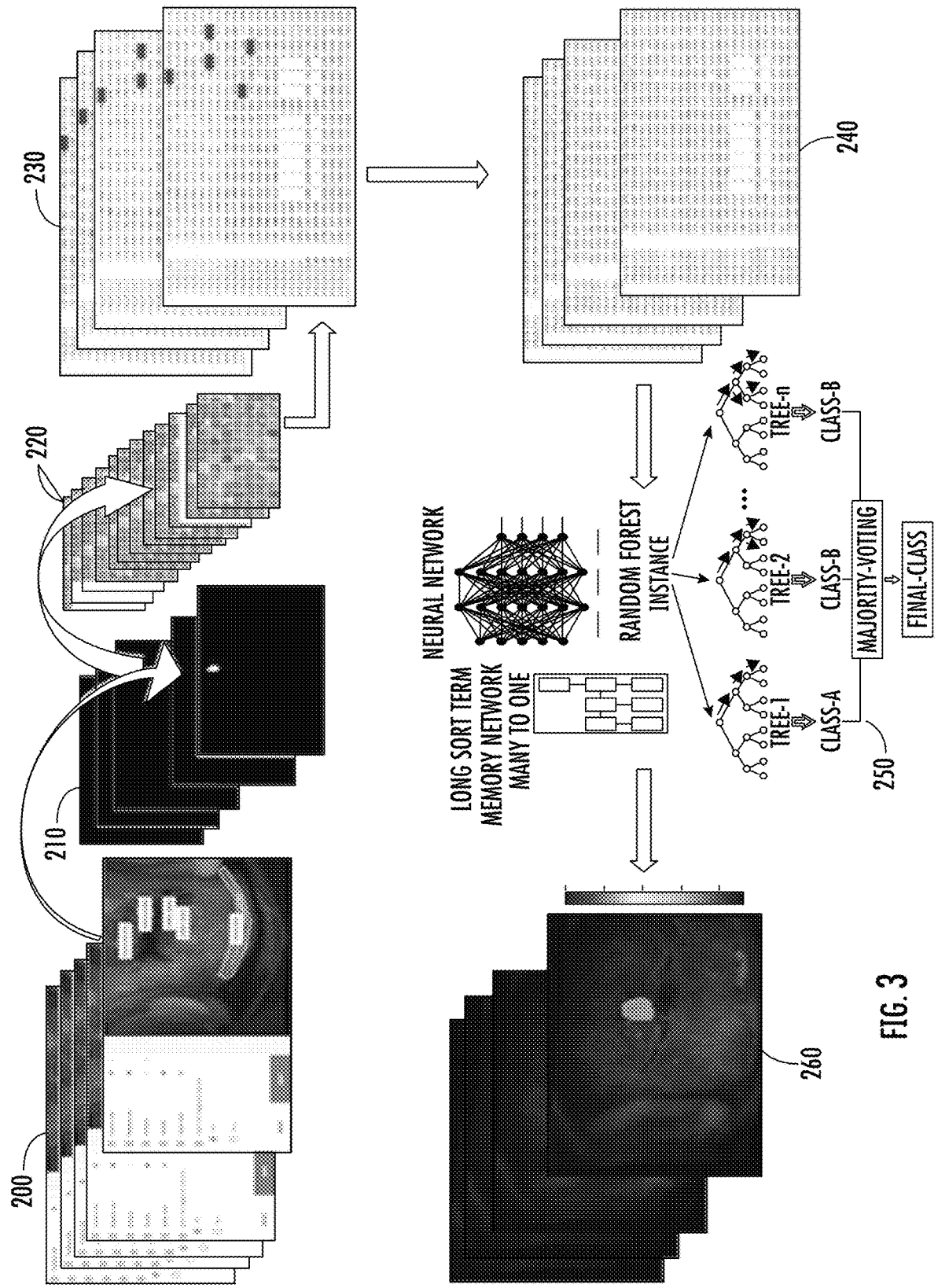
FIG. 3 illustrates schematically a flowchart illustrating a methodology for an experimental system in accordance with the disclosure.

Experimental results will now be discussed. The experiments performed are explained with reference to FIG. 3, in which there is illustrated schematically a flowchart detailing a methodology for the experimental system. This flowchart indicates a working pipeline, subsequent to a step of selection of patient datasets that meet basic quality criteria (such as well-focused images, complete image sequence, no significant artefacts and known biopsy results). Firstly, annotation of the images for training 200 (marking of biopsy areas and appending disease labels to them) was carried out by reviewing the images and videos of the biopsy procedure for accurate placement of the labels on the tissue. This was followed by mask generation 210 comprising extraction of corresponding image masks. Extraction of patches 220 was then performed across 17 time-points. Feature extraction 230 comprises extracting features from each biopsy area and separately for all patches. A data imputation technique 240 was then performed to account for any missing values. Deep learning scheme step 250 comprises set-up and training of three different machine learning schemes for the calculation of probabilities for each patch. Finally, heat-map generation 260 results from the outputs of the deep learning schemes for the test cases. The test cases were prepared in a similar way to that described by the methodology of FIG. 3. The only difference was that the models did not know the disease status of the biopsy area (that is, in the annotation 200), but had to predict it instead.

The dataset originated from an existing clinical trial using a digital colposcope manufactured by DYSIS Medical Limited, with Dynamic Spectral Imaging (DSI) mapping and including 222 patients with 396 independent biopsies. The locations of the biopsies were known and biopsies included visually selected biopsies, biopsies based on the DSI map and random biopsies from areas that appeared normal to the clinician. The dataset of each patient comprised 17 images, which include a reference image (pre-acetowhitening) and 16 subsequent images at standard time points. The images used as input are after they had been registered (aligned) to compensate for movements (displacements, contractions or the like).

For a binary classification of results, biopsies were divided according to their histological grading into two classes: Normal/Low Grade—NLG (including Negative and CIN1 results) as a "negative" class; and High Grade—HG (CIN2, CIN3, AIS, Invasive cancer) as a "positive" class. This is a clinically meaningful classification and consistent with that used in most colposcopy studies.

The dataset was manually split by patient into 80% for training set, 10% for validation and 10% for independent testing. For this split, the number of biopsies per patient and the percentage of low-grade and high-grade biopsies was considered, in order to create similar patient distributions within the validation and test sets. The remaining patients were used for training. The training set included 172 patients and 306 biopsies, the validation included 25 patients and 46 biopsies, and the test set included 25 patients and 44 biopsies.

The biopsy areas of each image were individually annotated (spatially marked and labelled with grade of disease). Each biopsy was categorized according to its histopathological grade as Normal, CIN1, CIN2, CIN3, AIS or Invasive cancer.

Following the annotation, the corresponding masks (that is, image area) of each biopsy were extracted. Based on these masks, patches were extracted across the 17 aligned images for the different time points. The patches were initially extracted with different sizes 16×16, 32×32 and 64×64 pixels and with different strides of 8, 16, 32 and 64 pixels to allow exploring which combinations worked best.

From each patch, a multitude of hand-crafted features, based on local colour, gradient and texture were extracted to be applied as input in the machine learning algorithms (see: Tao Xu et al, Pattern Recognit. 2017 March; 63: 468-475; Kim E, Huang X. "A data driven approach to cervigram image analysis and classification", Color Medical Image analysis, Lecture Notes in Computational Vision and Biomechanics. 2013; 6:1-13; and Song D, Kim E, Huang X, et al. "Multi-modal entity coreference for cervical dysplasia diagnosis", IEEE Trans on Medical Imaging, T M I. 2015; 34(1):229-245). This resulted in a total of 1,374 features for each patch and time-point. The features that were extracted were highly varying in value magnitudes, units and range, so they were all normalized on a 0-1 scale:

$$x' = \frac{x - \min(x)}{\max(x) - \min(x)}.$$

After feature extraction, data imputation was applied (see G. Welch, G. Bishop, "An Introduction to the Kalman Filter", SIGGRAPH 2001 Course 8, 1995) to compensate for some missing features on blurry and misaligned patches. The imputation method was validated separately. The data was structured so that for each patient, a matrix was provided of the time points from each patch extracted from the biopsy area(s) against the values of each of the extracted features (including the imputed ones) for each of the patches.

The machine learning models used in the analysis are now discussed. The data as described above was used as input to three different machine learning classifiers: Random Forest (RF); fully connected Neural Network (fNN); and a Long Short-Term Memory Neural Network (LSTM, that is a type of a Recurrent Neural Network, RNN).

Figure 4:
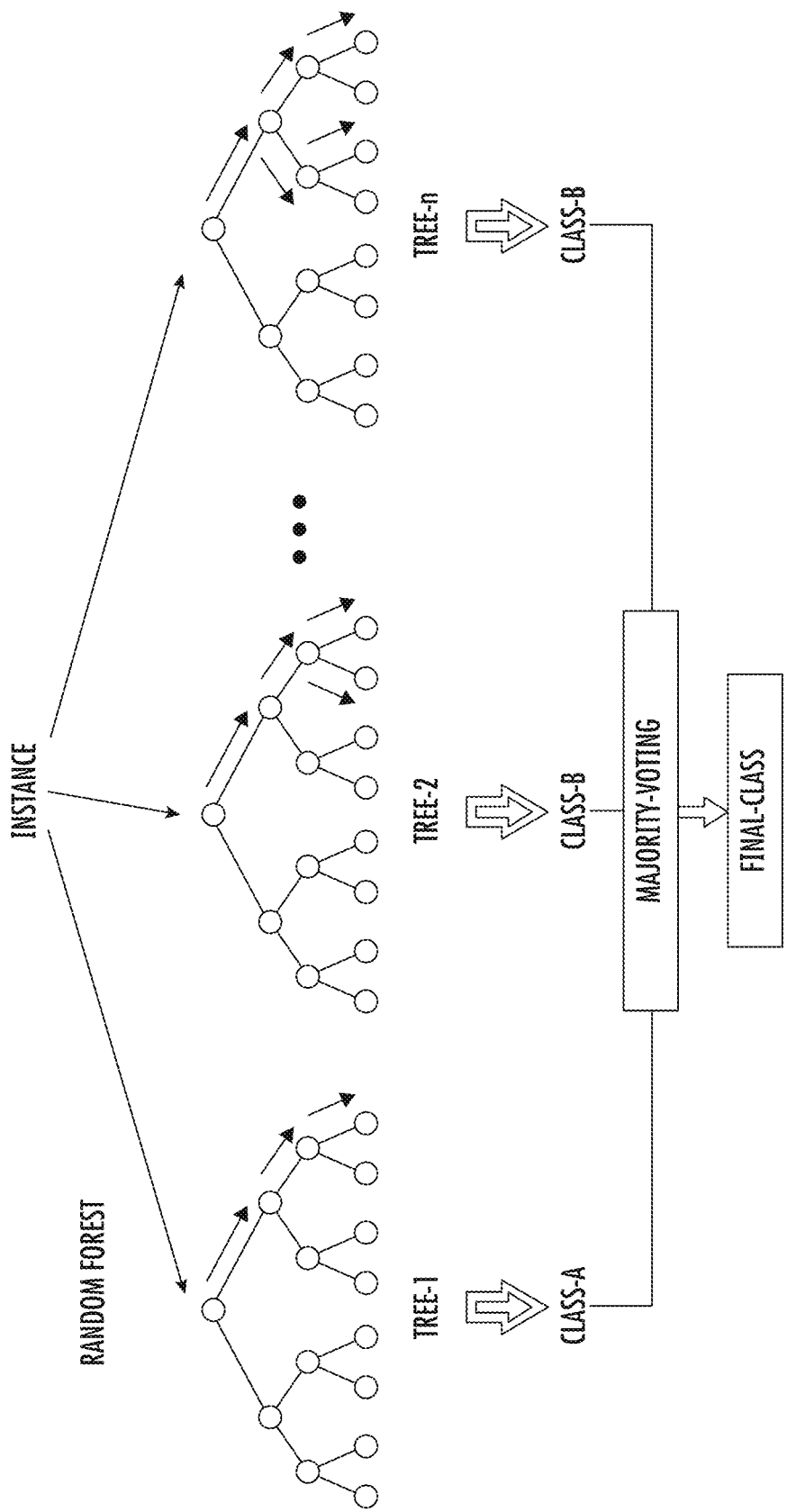
FIG. 4 schematically depicts a known random forest classification model.

Referring next to FIG. 4, there is schematically depicted a known random forest classification model. Random forests or random decision forests are an ensemble learning method for classification, regression and other tasks that operates by constructing a multitude of decision trees at training time and outputting the class that is the mode of the classes (classification) or mean prediction (regression) of the individual trees (see Ho, Tin Kam, "Random Decision Forests", Proceedings of the 3rd International Conference on Document Analysis and Recognition, Montreal, QC, 14-16 Aug. 1995. pp. 278-282). Random decision forests correct for the tendency of decision trees of overfitting to their training set. To implement the Random Forest (RF) classifier, a scikit-learn Python library and 150 estimators (decision trees) was used.

Figure 5:
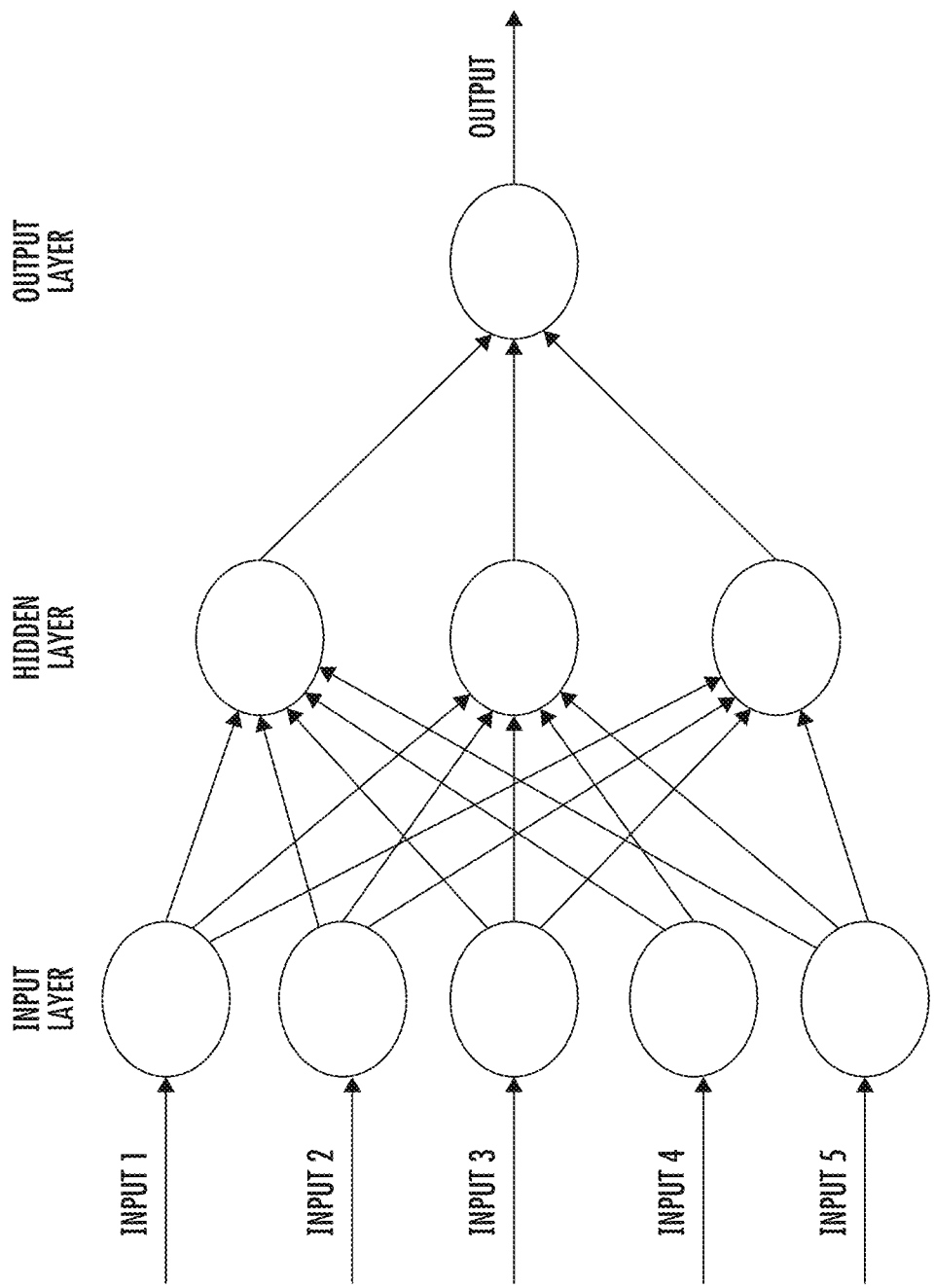
FIG. 5 schematically shows a known artificial neural network architecture.

Referring now to FIG. 5, there is schematically shown a known Artificial Neural Network (ANN) architecture. An ANN (also termed a Neural Network or NN) is an information processing paradigm that is inspired by the way biological nervous systems, such as the brain, process information. The key element is the novel structure of the information processing system. It is composed of a large number of highly interconnected processing elements (neurons) working in unison to solve specific problems. NNs, like people, learn by example. A NN is configured for a specific application, such as pattern recognition or data classification, through a learning process. Learning in biological systems involves adjustments to the synaptic connections that exist between the neurons. This is true of NNs as well.

Neural networks, with their ability to derive meaning from complicated or imprecise data, can be used to extract patterns and detect trends that are too complex to be noticed by either humans or other computer techniques. A trained neural network can be thought of as an "expert" in the category of information it has been given to analyse. This expert can then be used to provide projections given new situations of interest and answer "what if" questions. For the case of Neural Networks, the open source machine learning framework TensorFlow® Python was employed. After a hyper-parameter tuning and a small grid search, a fully connected network with 3 layers and 50 units each and with a softmax layer with 2 units as output layer was used.

Although a NN can be a useful tool for such classification, it has been recognised that humans do not start their thinking from scratch in every circumstance. Traditional NNs cannot use information from previous training, which seems a shortcoming. Recurrent Neural Networks (RNN) address this issue. They are networks with loops in them, allowing information to "persist". A RNN can be thought of as multiple copies of the same network, each passing a message to a successor.

Figure 6:
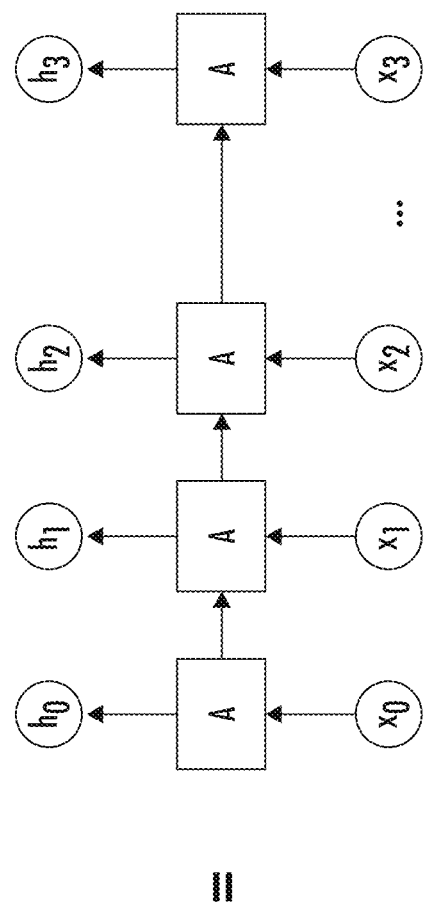
FIG. 6 schematically illustrates a known long sort term memory architecture.
Figure 6:
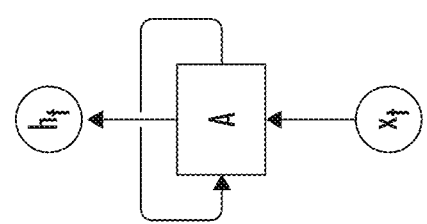

Reference is next made to FIG. 6, in which there is schematically illustrated a known Long Sort Term Memory (LTSM) basic architecture. LSTMs are a special kind of RNN, capable of learning long-term dependencies. LSTMs are explicitly designed to avoid the long-term dependency problem. The same process as in ANN is used for classifier implementation for the case of LSTM. More specifically, after the hyperparameter optimization and the grid search, the best model was found to consist of: two LSTM layers with 20 units each; and softmax with 2 units as output layer.

In addition, a series of ensemble classification schemes were developed, using the average of the probabilities for each patch of all possible combination of the three classifiers. Specifically, four combinations were tested for RF+NN+LSTM, RF+NN, RF+LSTM and NN+LSTM for the 25 test patients for biopsies.

A series of weighted average probabilities schemes were also developed. More specifically, a "shallow neural network" was trained with combined validation probabilities according to each ensemble scheme, while the validation probabilities were extracted individually from each prime model above (RF, NN and LSTM). In contrast with a Deep NN, a shallow NN has only one hidden layer.

The architectures were initially trialled at different combinations of patch size and stride, to evaluate which approach would work best given the size of the image masks and the features. The combination of patch size 32×32 with a stride of 8 pixels was found to work best, so was adopted for the fine-tuning of all models and the generation of results.

The performance of each of the tested approaches is now discussed with reference to FIGS. 7A to 7D and 8A to 8D, in which there are shown indicative heat-maps for example biological tissues processed. The patch-level probabilities that are calculated by the three basic classifiers (RF, NN and LSTM) for the image masks (i.e. biopsy areas) in the test set were used to construct the corresponding heat-maps shown. The models had not "seen" these cases before and did not know their outcomes. The probability assigned to each pixel of the heat-map was the average of its value in all the patches that included it. Indicatively, heat-maps for two out of 25 test cases are presented, each using three different machine learning techniques (FIGS. 7B, 7C, 7D and FIGS. 8B, 8C, 8D), together with the corresponding DSI map from the original examination (FIGS. 7A and 8A).

For the clinical evaluation of the classification, the predictions for each biopsy area by each method were categorized into two classes: NLG (normal or low grade) and HG (high grade). This was done case-by-case by visual assessment and if a biopsy heat-map contained probabilities greater than 0.5 (that is red, yellow or white colour), then the prediction for this biopsy was categorized as HG, otherwise it was considered NLG.

Figure 7:
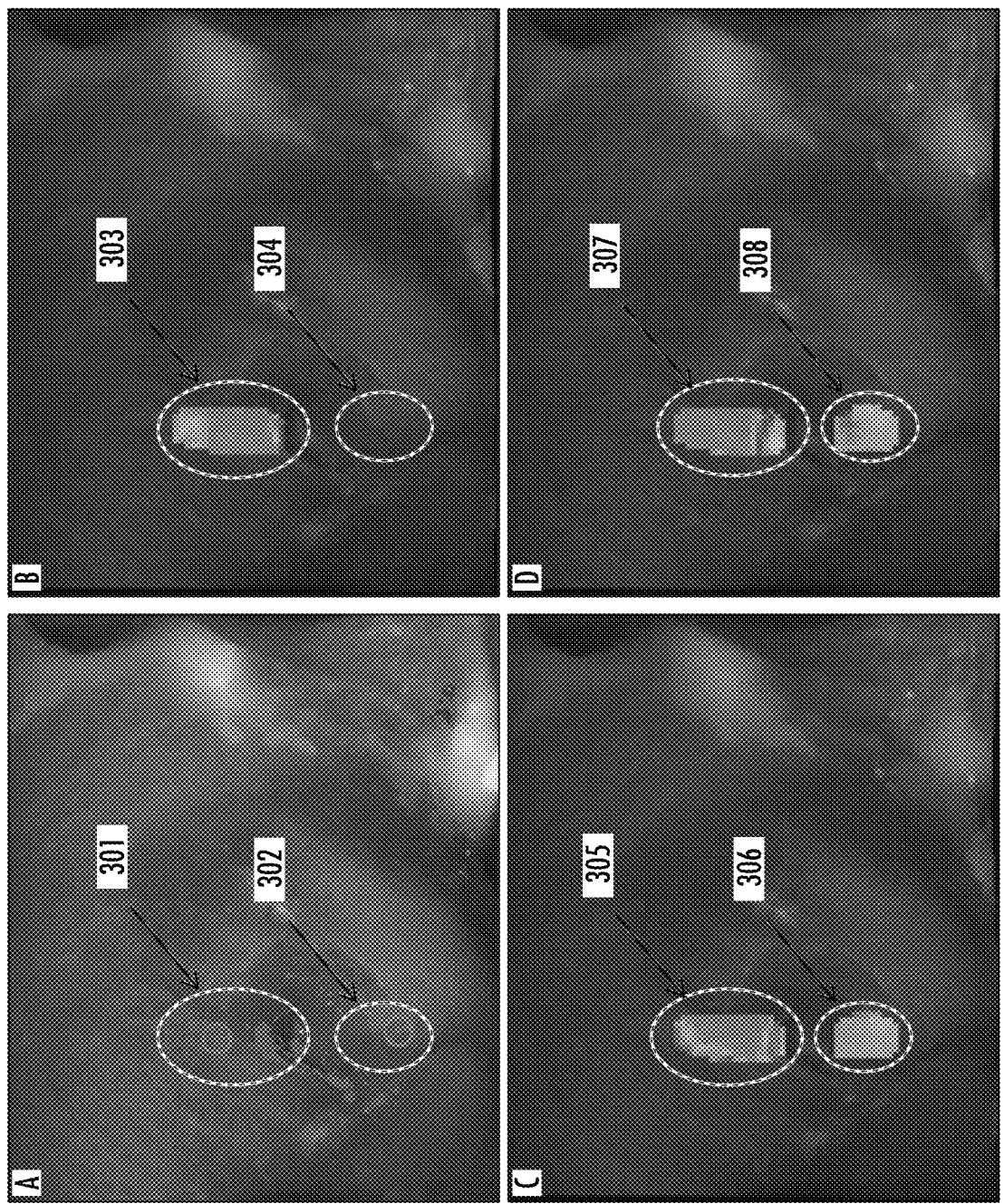
FIGS. 7A, 7B, 7C and 7D each show indicative heat-maps for first example biological tissues processed by an existing method (FIG. 7A) or in accordance with the methodology of FIGS. 4 to 6 (FIGS. 7B, 7C and 7D)

Referring first to FIG. 7A, region 301 shows a biopsied area with a high grade (HG) result and region 302 shows a biopsied area with a negative/low grade (NLG) result (the status of the biopsied tissues was confirmed by histological grading). The smaller circle annotations within the biopsied areas (regions 301 and 302) represent clinician annotations from an original examination. The DSI map had failed to highlight the area at region 301 as potential HG, and had correctly classified region 302 as normal/low grade. Referring to FIG. 7B, there is shown a heat-map with the outputs of a RF algorithm, as discussed above. Here, a high probability region 303 is identified in the same region as region 301, but nothing appears at region 304, which is the same tissue area as region 302. Referring to FIG. 7C, there is shown a heat-map with the outputs of a NN algorithm, as discussed above. A high probability region 305 is identified in the same tissue area as region 301 and a low probability region 306 is identified in the same tissue area as region 302. Referring to FIG. 7D, there is shown a heat-map with the outputs of a LSTM algorithm, as discussed above. A clearer high probability region 307 is identified in the same tissue area as region 301 and a clearer low probability region 308 appears in the same tissue area as region 302. This shows an improvement in performance of the three machine learning algorithms relative to the standard DSI algorithm, as they correctly highlighted the area of HG biopsy result and also predicted the area of NLG biopsy result correctly.

Figure 8:
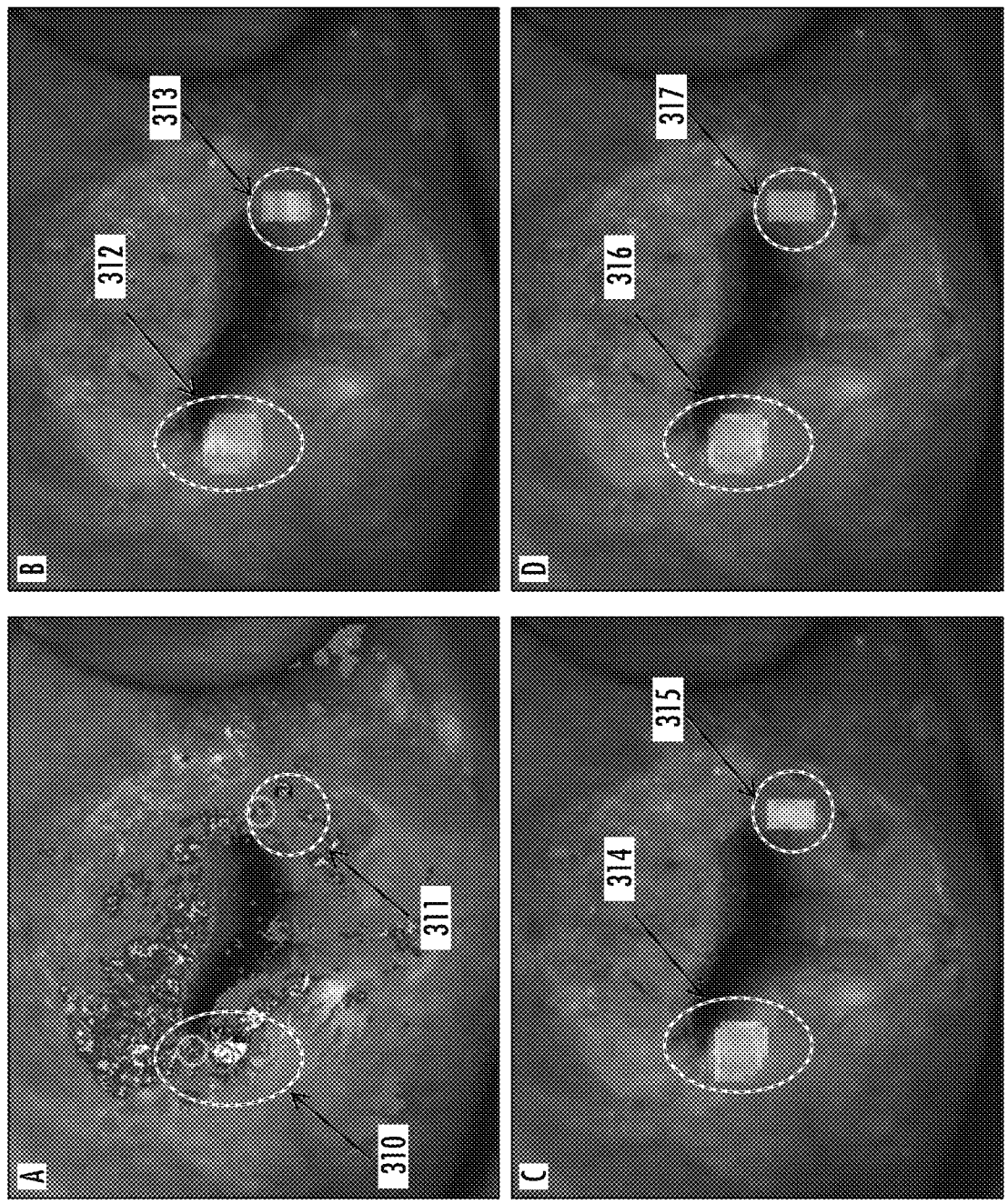
FIGS. 8A, 8B, 8C and 8D each show indicative heat-maps for second example biological tissues processed by an existing method (FIG. 8A) or in accordance with the methodology of FIGS. 4 to 6 (FIGS. 8B, 8C and 8D).

Referring to FIG. 8A, there are shown two biopsied areas 310 and 311 that were both high grade (HG). The smaller circle annotations within (or intersecting) the biopsied areas 310 and 311 represent clinician annotations from an original examination. The status of the biopsied tissues was confirmed by histological grading. The DSI map had highlighted one of the two regions (biopsied area 310) as potential HG but had failed to highlight region 311 as HG. Referring to FIG. 8B, there is shown a heat-map with the outputs of a RF algorithm, as discussed above. Here, a high probability region 312 is identified in the same region as one of the HG biopsied areas and a somewhat lower probability region 313 is identified in the same region as the other of the HG biopsied areas. Referring to FIG. 8C, there is shown a heat-map with the outputs of a NN algorithm, as discussed above. A high probability region 314 is identified in the same region as one of the HG biopsied areas and a lower probability region 315 is identified in the same region as the other of the HG biopsied areas. Referring to FIG. 8D, there is shown a heat-map with the outputs of a LSTM algorithm, as discussed above. A high probability region 316 is identified in the same region as one of the HG biopsied areas and a high probability region 317 also appears in the same region as the other of the HG biopsied areas. The improvement in performance of the LSTM algorithm is therefore seen relative to the RF and NN algorithms, as well as the original DSI algorithm.

Given the relatively small number of cases and the unbalanced nature of the dataset, to summarize the performance with one overview metric, the "balanced accuracy" is used to classify a) the biopsies and b) the patients correctly as Normal/Low-Grade vs. High-Grade. The balanced accuracy (referred to as simply accuracy below) is the average of the number of cases that have been correctly classified in each class. This is effectively the average between sensitivity and specificity and provides a more global overview than sensitivity and specificity alone.

On the biopsy-level analysis (that is, each biopsy considered and analysed as a separate unit), the accuracy of the RF and NN classifiers was 81%, whereas for the LSTM it was 84%. For comparison, on the same dataset, the original DSI map achieved a 57% accuracy. For a patient-level analysis based on the results of the biopsy areas, each patient was considered as HG when at least one biopsy was HG. The RF and NN achieved a 77% accuracy, LSTM achieved 70%, whereas the accuracy of the original DSI map was 59%.

The accuracy for the biopsy-level analyses of the Average Ensemble schemes ranged from 77% (RF+NN) to 83% (RF+LSTM, NN+LSTM and RF+NN+LSTM). For the patient-level analyses, the accuracy of all schemes was 81%. The accuracy for the biopsy-level analyses of the Weighted Average Ensemble schemes was 77% (RF+NN+LSTM), 79% (RF+LSTM), 86% (RF+NN) and 88% (NN+LSTM). For the patient-level analyses the accuracy of the schemes was 77% (RF+NN+LSTM and RF+NN) and 81% (RF+LSTM and NN+LSTM).

The machine learning models that were developed in this proof-of-concept project achieve an overall improved performance than the existing DSI map in mapping and classifying tissue areas as Normal/Low-Grade vs High-Grade, demonstrating a clinical application that can be used to further improve the support of biopsy site selection and clinical management decisions.

Including larger datasets for training and testing of the models may be beneficial. Different selection of features and patch size effects may also be considered. Additional data and risk-factors that are available for each patient are the colposcopy illumination brightness setting at the original collection of images and the patient age, screening results (cytology, hrHPV, HPV16, HPV18) and smoker status. These may also be used as input to the models, which may boost performance further.

When trained on a large dataset, the models may be used to calculate heat-maps not only for biopsy areas, but for the entire cervix and also accommodate for the existence of artefacts.

The features used for training of the models in the experiment described above were extracted from each time point separately and their time-dependence was assumed to be picked up by the networks. In another embodiment, the design of features to extract could include the time element, so that a feature is a function of a characteristic across time.

The use of Convolutional Neural Networks (CNN) either independently or as part of an ensemble scheme is also possible, for example the combination of RNN with CNN. The key module of this scheme may be the recurrent convolution layers (RCL), which introduce recurrent connection into a convolution layer. With these connections, the network can evolve over time though the input is static and each unit is influenced by its neighbouring units. Another example is the use of a CNN with a single time-point image as input that will generate a classification probability for the patient. This has been shown to be able to generate accurate results that may then be fed into another neural network classifier (for example, NN or RNN) as an additional input together with the image sequence. Yet another example is the use of distinct CNNs to evaluate each individual image in the sequence separately and the combination of their individual outputs into another neural network, for example an RNN or an LSTM to provide the final output. The utilization of CNNs may not require the extraction of hand-crafted features, as described above, since features may be extracted by the network itself.

Although specific embodiments have now been described, the skilled person will appreciate that various modifications and alternations are possible. For instance, including different types of image processing and machine learning classifiers in various schemes may be considered. As noted above, the disclosure is generally directed towards examination of cervical tissue using an aceto-whitening process, but may be implemented for examination and/or classification of other biological tissues using a pathology differentiating agent. For example, although dilute acetic acid is preferably used, other types of acid may be used instead for particular purposes. The technique may also be suitable for classification using molecular diagnostics. Whilst the preferred embodiment uses in-vivo captured images, implementations that use in-vitro captured images may also be considered. In some embodiments, an incomplete dataset for a patient may be provided as an input to the AI.

A specific arrangement of local and remote processors has been disclosed, but the skilled person will appreciate that different processor arrangements are possible. For example, one or multiple processors may only be provided locally to the image capture module. Alternatively, one or multiple processors may only be provided remotely to the image capture module. A computer cloud-based analysis or non-cloud based analysis may be employed. In particular, an implementation may be considered with first and second machine learning algorithms provided remotely to the image capture module, with the first machine learning algorithm being fixed and the second machine learning algorithm have continual training (in the manner described above).

Different type of neural network structures or machine learning algorithms may be envisaged. Structures of machine learning algorithms may be uni-modal (taking only image data as an input) or multi-modal (taking both image data and non-image data as inputs). Although the results of the AI (that is, an output image) are displayed as a probabilistic heat map above, other outputs (in data formats or visualizations) may be possible.

The invention claimed is:

1. A method for classification of a biological tissue using a computing system, the method comprising:
   obtaining a set of raw time-series images of an examination area of the biological tissue, wherein the set of raw time-series images corresponds to a discrete time period in which portions of the biological tissue undergo a transient optical response responsive to topical application of a pathology differentiating agent to the biological tissue;
   obtaining time data associated with the set of raw time-series images;
   processing the set of raw time-series images to create a modified set of time-series images such that they are aligned with respect to each other;
   extracting a set of pixel values against time for multiple pixels from the modified set of time-series images and the time data;
   inputting the set of pixel values against time for multiple pixels into an algorithm that identifies segments of the biological tissue based on analysis indices that are derived from a curve of intensity value against time for each pixel, the identified plurality of segments of the biological tissue being obtained as an output of the algorithm;
   inputting the set of pixel values against time for multiple pixels and the identified plurality of segments of the biological tissue into a trained neural network that characterizes a likelihood that portions of the biological tissue correspond to a disease state or lesion, the trained neural network being separate from the algorithm that identifies the plurality of segments of the biological tissue;

obtaining one or more classifications of each of the plurality of segments of the biological tissue from the trained neural network; and outputting a cancer assessment for at least one of the plurality of segments based on the one or more classifications output by the trained neural network, wherein the cancer assessment indicates one of a precancerous disease state, a cancerous disease state, or a non-cancerous state.

2. The method of claim 1, wherein the processing comprises applying one or more transformations to each raw time-series image including displacing, scaling, deforming or rotating to create the modified set of time-series images.

3. The method of claim 2, wherein one or more of:
the biological tissue comprises a cervix uteri, or
each of the modified set of raw time-series images is derived from a respective initial image processed to remove one or more artefacts.

4. The method of claim 1, wherein:
at least one image of the set of raw time-series images is captured at a start of the discrete time period, prior to the transient optical response occurring; and
at least some of the set of raw time-series images are captured at intervals of a predetermined duration during the topical application of the pathology differentiating agent.

5. The method of claim 1, wherein:
the biological tissue comprises a cervix uteri;
the examination area is exposed to optical radiation during the discrete time period;
the pathology differentiating agent comprises an acid; and
said obtaining the set of raw time-series images comprises capturing a plurality of optical images of the examination area of the biological tissue using an image collection module, the set of raw time-series images being derived from the plurality of optical images.

6. The method of claim 1, further comprising:
processing the set of raw time-series images or modified set of time-series images to identify at least one morphological characteristic and/or at least one extracted feature.

7. The method of claim 6, wherein the at least one morphological characteristic and/or at least one extracted feature is identified by the trained neural network.

8. The method of claim 1, wherein the trained neural network comprises a deep neural network and/or at least one of a convolutional neural network, a fully-connected neural network, or a recurrent neural network.

9. The method of claim 1, further comprising:
obtaining a set of subject characteristics, wherein each subject characteristic corresponds to a subject from which the biological tissue originates, and wherein each subject characteristic relates to at least one of medical history information, risk factor information, or clinical test result information; and
inputting the set of subject characteristics into the trained neural network in addition to the set of pixel values against time for multiple pixels and the identified plurality of segments of the biological tissue, wherein the trained neural network characterizes the likelihood that the biological tissue corresponds to a disease state based on the set of subject characteristics.

10. The method of claim 9, wherein the one or more subject characteristics comprises the risk factor information, the medical history information, and the clinical test result information.

11. The method of claim 10, wherein the risk factor information comprises at least one of an age of the subject, a smoker status of the subject, a prior HPV vaccination status of the subject, information on use of condom during intercourse for the subject, or a parity for the subject; and
wherein the clinical test result information comprises at least one of a prior cytology result, a prior HPV test result, a prior HPV typing test result, a prior cervical treatment information, or a prior history of screening for and/or diagnosis of cervical cancers or pre-cancers.

12. The method of claim 1, further comprising:
allocating one of the one or more classifications obtained from the trained neural network to an entire portion of the biological tissue based on a different trained neural network.

13. The method of claim 1, wherein the one or more classifications indicate a presence of at least one morphological characteristic.

14. The method of claim 1, wherein the trained neural network was previously trained based on another set of raw time-series images, a respective allocated classification for each of a plurality of other biological tissues, and/or a user-determined or database classification.

15. The method of claim 1, wherein the trained neural network is a first trained neural network, and wherein said outputting the cancer assessment is performed using a second trained neural network that is different from the first trained neural network.

16. The method of claim 1, wherein the one or more classifications comprise a plurality of grades.

17. The method of claim 1, wherein said processing the set of raw time-series images comprises processing each pixel within the set of raw time-series images.

18. The method of claim 1, wherein said analysis indices represent at least one measure of diffuse reflectance.

19. The method of claim 1, wherein obtaining the set of raw time-series images comprises capturing images across a spectrum of visible light that includes red, green, and blue (RGB) channels.

20. The method of claim 1, wherein the trained neural network determines an individual transient optical response for each pixel of the multiple pixels.

21. The method of claim 20, wherein the trained neural network outputs a heat map based on the individual transient optical responses, wherein each pixel in the heat-map corresponds to a specific location in the biological tissue and a respective likelihood of the disease state.

22. The method of claim 14, wherein the user-determined or database classification comprises one or more of: histology results; clinical assessments; and expert annotations.

23. A non-transitory computer-readable medium storing instructions that, when executed by a processor, cause the processor to:
obtain a set of raw time-series images of an examination area of a biological tissue, wherein the set of raw time-series images corresponds to a discrete time period in which portions of the biological tissue undergo a transient optical response responsive to topical application of a pathology differentiating agent to the examination area of the biological tissue;
obtain time data associated with the set of raw time-series images;

process the set of raw time-series images and the time data to create a modified set of time-series images such that they are aligned with respect to each other;

extract a set of pixel values against time for multiple pixels from the modified set of time-series images and the time data;

input the set of pixel values against time for multiple pixels into an algorithm that identifies segments of the biological tissue based on analysis indices that are derived from a curve of intensity value against time for each pixel, the identified plurality of segments of the biological tissue being obtained as an output of the algorithm;

input the set of pixel values against time for multiple pixels and the identified plurality of segments of the biological tissue into a trained neural network that identifies a plurality of segments of the tissue and characterizes a likelihood that the biological tissue corresponds to a disease state, the plurality of segments being identified based on common disease state, the trained neural network being separate from the algorithm that identifies the plurality of segments of the biological tissue;

obtain one or more classifications of each of the plurality of segments of the biological tissue from the trained neural network; and output a cancer assessment for at least one of the plurality of segments based on the one or more classifications output by the trained neural network, wherein the cancer assessment indicates one of a precancerous disease state, a cancerous disease state, or a non-cancerous state.

24. A computing system operative for classification of a tissue, comprising a processor configured to:

obtain a set of raw time-series images of an examination area of a biological tissue, wherein the set of raw time-series images corresponds to a discrete time period in which portions of the biological tissue undergo a transient optical response responsive to topical application of a pathology differentiating agent to the examination area of the biological tissue;

obtain time data associated with the set of raw time-series images;

process the set of raw time-series images and the time data to create a modified set of time-series images such that they are aligned with respect to each other;

extract a set of pixel values against time for multiple pixels from the modified set of time-series images and the time data;

input the set of pixel values against time for multiple pixels into an algorithm that identifies segments of the biological tissue based on analysis indices that are derived from a curve of intensity value against time for each pixel, the identified plurality of segments of the biological tissue being obtained as an output of the algorithm;

input the set of pixel values against time for multiple pixels and the identified plurality of segments of the biological tissue into a trained neural network that identifies a plurality of segments of the tissue and characterizes a likelihood that the biological tissue corresponds to a disease state or lesion, the trained neural network being separate from the algorithm that identifies the plurality of segments of the biological tissue;

obtain one or more classifications of each of the plurality of segments of the biological tissue from the trained neural network; and output a cancer assessment for at least one of the plurality of segments based on the one or more classifications output by the trained neural network, wherein the cancer assessment indicates one of a precancerous disease state, a cancerous disease state, or a non-cancerous state.

25. The computing system of claim 24, further comprising:

an image collection module configured to capture the set of raw time-series images.

26. The computing system of claim 25, wherein:

the image collection module is located remotely from a processor on which the trained neural network is operated.

* * * * *

UNITED STATES PATENT AND TRADEMARK OFFICE
CERTIFICATE OF CORRECTION

| | | |
|---|---|---|
| PATENT NO. | : 12,002,573 B2 | Page 1 of 1 |
| APPLICATION NO. | : 18/046249 | |
| DATED | : June 4, 2024 | |
| INVENTOR(S) | : Papagiannakis et al. | |

It is certified that error appears in the above-identified patent and that said Letters Patent is hereby corrected as shown below:

On the Title Page

Please add: (30) Foreign Application Priority Data:
Jul. 24, 2018 (GB)..........................1812050.1

Signed and Sealed this
Thirtieth Day of July, 2024

Katherine Kelly Vidal
*Director of the United States Patent and Trademark Office*